United States Patent [19]
Markart

[11] Patent Number: 5,889,585
[45] Date of Patent: Mar. 30, 1999

[54] METHOD AND APPARATUS FOR THE MEASUREMENT OF BLOOD SUGAR

[75] Inventor: Ernst Markart, Munich, Germany

[73] Assignee: LRE Technology Partner GmbH, Munich, Germany

[21] Appl. No.: 936,644

[22] Filed: Sep. 24, 1997

[30] Foreign Application Priority Data

Sep. 24, 1996 [DE] Germany .......................... 196 39 227.6

[51] Int. Cl.⁶ .................................................. G01N 33/48
[52] U.S. Cl. .............................................. 356/39; 356/446
[58] Field of Search ...................... 356/39–42, 445–448, 356/73; 436/164–172; 422/58, 82.05, 82.09

[56] References Cited

U.S. PATENT DOCUMENTS 4,676,653  6/1987  Strohmeier et al. ..................... 356/446
5,580,794  12/1996  Allen ........................................ 436/169

*Primary Examiner*—Robert Kim
*Attorney, Agent, or Firm*—McCormick, Paulding & Huber

[57] ABSTRACT

In an apparatus and method for detecting the concentration of a substance in a fluid, such as the concentration of sugar in blood, the measuring field of a test strip to which the fluid to be tested in applied is divided into two separate measuring areas. The change in the light reflection or light transmission capacity of the two measuring areas is then detected separately at repetitive time intervals, and in comparing the changes in light reflectivity or light transmission of the two measuring areas over time, perceived differences in the changes occurring in the two areas are evaluated to provide useful information.

7 Claims, 3 Drawing Sheets

METHOD AND APPARATUS FOR THE MEASUREMENT OF BLOOD SUGAR

FIELD OF THE INVENTION

The invention concerns a method for measuring the concentration of a substance in a fluid, especially for blood sugar measurement, wherein the liquid to be measured is applied to a measuring field, made of a hydrophilic material, of a test strip, and the effect of that application in changing the optical reflection or transmission capacity in the area of the measuring field is determined.

BACKGROUND OF THE INVENTION

In the case of blood sugar measurements performed by patients themselves, the patient gives a drop of blood onto the measuring field of a test strip which is then optically measured, with the detector, for example, detecting the color change of the measuring field which is provoked by the application of the blood to the measuring field. The signal produced by the detector corresponds to an average value of the color change in the measuring field. A correct value is thereby obtained only if the amount of blood is sufficient to uniformly wet the entire measuring field. If, in contrast to this, the measuring field is only partially wetted, the measurement becomes falsified since in the making up of the measured value, areas are also included in which practically no chemical reaction results and, therefore, in which no color change takes place. By the time this error is recognized in a customary measurement, a subsequent dosing as a rule is no longer possible because, in the wetted portion of the measuring field, the chemical reaction has already so far advanced that upon further application of blood a uniform coloring of the measuring field is no longer achievable. Moreover, in the case of the patient, as a rule, the small stab wound from which the blood drops have been pressed has again so far closed that no further blood can escape. The patient must, therefore, repeat the measurement, which for him can be very uncomfortable if one remembers that a patient, depending on circumstances, must carry out such measurement several times a day and with each measurement must each time stick himself in the finger.

The invention has as its object the provision of a method of the aforegoing type in which the previously mentioned error can be recognized in time and can be eliminated in the same measurement.

SUMMARY OF THE INVENTION

The object is solved in accordance with the invention in that the measuring field is divided into at least two measuring areas, which measuring areas are separately sensed, and that an indicator is actuated if after a pre-given time the difference for the two measuring areas produces a measured value which exceeds a pre-given value.

If the measured values in the two measuring areas are distinctly different, so that their difference exceeds a pre-given threshold value, this indicates that the measuring field has not been uniformly wetted by the fluid under investigation and the chemical reaction provoked by the application of the fluid to the measuring field, which, for example, effects a measurable color change, has not progressed uniformly in the two measuring areas. One can then select a time for such a test of the measured values that a subsequent application is still possible. In the use of customary measuring strips with the measuring procedure of the invention, for example, after five seconds it can be determined whether the measuring field has been uniformly wetted by the fluid under investigation. If this is not the case, the patient is alerted, so that he can again apply a dosage. Within this short time, it is generally also possible to again press blood from the same stab wound. Further, the chemical reaction in the wetted areas have not yet so far progressed that a subsequent dosing is no longer possible.

With the process of the invention, one can also determine whether a test strip is correctly inserted into the measuring device, for example, pushed in up to a stop. Only if the test strip assumes its correct measuring position will both measuring areas lie in the measuring field. By suitable coloring of the surroundings of the measuring field assurance can be obtained that the same or nearly the same measuring values in the two measuring areas can only be obtained if both measuring areas lie inside of the measuring field. If, therefore, in a measurement, the indicator is actuated, the user should investigate whether the measuring strip has been correctly inserted into the measuring device.

The process of the invention can be carried out in such way that the two measuring areas are measured at the same pre-given time points and the measured values compared with one another. It is, however, also possible for each measuring area to measure the time required for the reflection or transmission capacity to reach a pre-given value with, upon the exceeding of a pre-given time interval, an indicator being actuated which invites the patient to apply a subsequent dosage.

In one embodiment of the inventive process, the change in the reflection or transmission capacity inside the measuring areas is determined over time and an indication is actuated if the sensed change of the reflection or transmission capacity deviates from a pre-given set value by more than a pre-given amount. This change of the reflection or transmission capacity over time, that is the speed of change can be determined by several measurements in short time intervals. By these measurements of speeds of change it can be determined whether the reactions in the measuring fields proceed correctly and, as the case may be, also which test strip has been inserted, that is which reaction is taking place. For different substances to be analyzed different test chemicals are used. The associated reactions distinguish themselves clearly in the speed of change of the reflection or transmission capacities.

The invention further concerns an apparatus for measuring the concentration of a substance in a liquid, especially for blood sugar measurement, by optical evaluation of a measuring field of a test strip containing the liquid to be measured, including a housing with a strip support for the test strip, a measuring optic system, an evaluation circuit, and an indicator unit. For the solution of the previously given object in a measuring device of the previously described type, in accordance with the invention, it is proposed that the measuring optic system have at least two detector units for detecting at least two different measuring areas. The detector units can, for example, each include a light emitter and a light receiving unit, which are directed onto different measuring areas and which are simultaneously actuatable. In another solution, the sensing units each have one light emitter with the light emitters being directed onto different measuring areas and being actuatable at different time points, for example, in alternation, and with the measuring field being sensed by one common detector of the detector unit.

BRIEF DESCRIPTION OF THE DRAWINGS

The following description explains the invention in connection with the accompanying drawings by way of exemplary embodiment. The drawings are.

DESCRIPTION OF THE PREFERRED EMBODIMENTS

Figure 1:
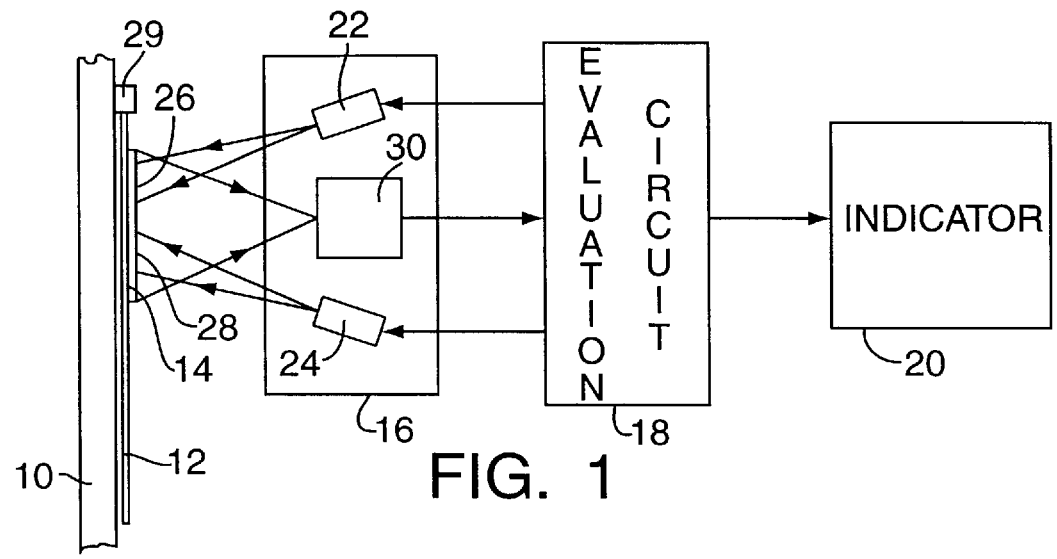
FIG. 1 a schematic representation of a measuring apparatus according to a first embodiment of the invention, FIG. 2 a schematic plan view of a portion of a test strip and of the measuring field, FIG. 3 a graphic representation of the reflection capacity versus time for dissimilarly wetted measuring areas of the measuring field, FIG. 4 a representation corresponding to FIG. 1 of a second embodiment of the measuring apparatus in accordance with the invention, and FIG. 5 a graphical representation corresponding to FIG. 3 for explaining a modified measuring method.
Figure 2:
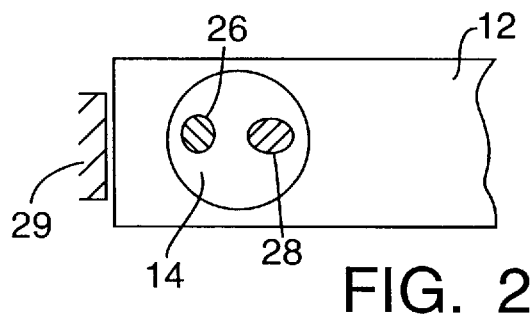

In the embodiment of the inventive measuring apparatus illustrated in FIG. 1, the apparatus comprises a strip support 10 for a test strip 12 having a measuring field 14, a measuring optic system 16, an evaluation and control circuit 18, and an indicator unit 20.

The measuring optic system 16 contains two light sources 22 and 24, which are provided by light-emitting diodes. The light sources 22 and 24 are directed onto different measuring areas 26 and 28 inside of the measuring field 14 of the test strip, when the test strip is positioned in the measuring device and against a stop 29. The light sources 22 and 24 are controlled by the evaluation and control circuit 18. The measuring optic system 16 further contains a detector 30 which receives light from the entire measuring field 14. The detector 30 is connected with the evaluation circuit 18.

In a blood sugar measurement, the patient applies a drop of blood onto the measuring field 14 of the test strip 12 and then lays the test strip in a pre-described position onto the strip support 10. In a customary measuring apparatus, the measuring field 14 is now illuminated and a detector receives the reflected light. Because of the applied blood and a chemical reaction with a test substance inside of the measuring field 14, the reflection capacity of the measuring field changes in a definite way. From the change in the reflection capacity, the blood sugar content can be determined by way of a characteristic curve stored in the evaluation circuit, which blood sugar content can then be indicated by the indicating device 20.

Figure 6:
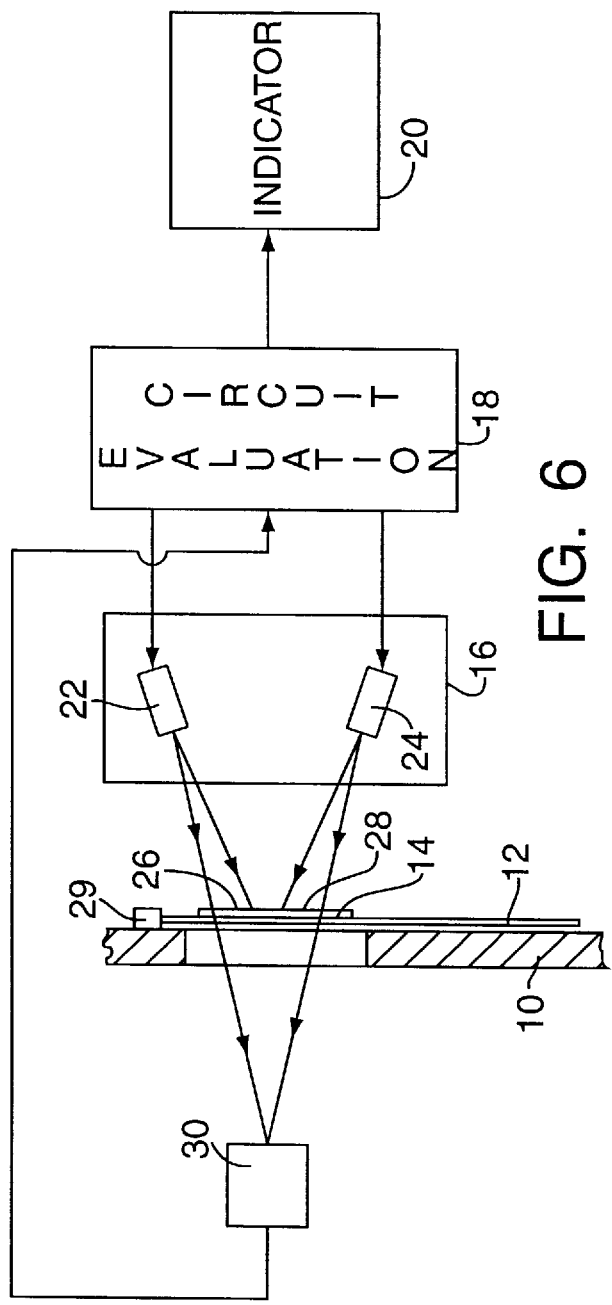
FIG. 6 a schematic representation of a measuring apparatus identical to that of FIG. 1 except for the detector receiving light transmitted through the measuring field rather than light reflected from the measuring field.

In the arrangement illustrated in FIG. 1, the light sources 22 and 24 are alternately switched on and off so that the detector 30 alternately receives light from the light spots 26 and 28. If the measuring field 14 is completely wetted by the applied blood, so that its reflection capacity is uniformly changed, no different results are obtained in comparison to the previously described customary measurement. However, if on the other hand, insufficient blood is applied to wet the entire measuring field 14, the reflection capacity in the measuring areas 26 and 28 changes in different ways. FIG. 6 shows the behavior of the reflection capacity (ordinate) in respect to time (abscissa). The two curves 32 and 34 give the different behaviors of the reflection capacity in the differently wetted areas 26 and 28. The value R1 corresponds to the empty value of the measuring field before the blood application. With the help of the evaluation circuit 18 now, for example, for both measuring areas 26 and 28, the times t1 and t2 which are required for the measured value R2 to be achieved in both of the measuring areas 26 and 28 can be measured. Whereas, in the ideal case, in which the entire measuring field 14 is uniformly wetted, the two curves 32 and 34 coincide and thereby produce no time difference for the two measuring curves, in the illustrated case, the measured value R2 for the two curves is reached in two different times t1 and t2. A threshold value for the time difference $\Delta t = t2-t1$ is predetermined. If this threshold value is exceeded, the evaluation circuit 18 produces a warning indication on the indicator unit 20. This signals the user that he should again apply blood to the measuring field 14 in order to be able to achieve a correct measurement. A second threshold value can also be determined for $\Delta t$, beyond which a further application of blood may no longer be made because the reaction caused by the first applied blood already has so far progressed that the subsequently applied blood can no longer produce a unified reaction inside of the measuring field 14.

Figure 3:
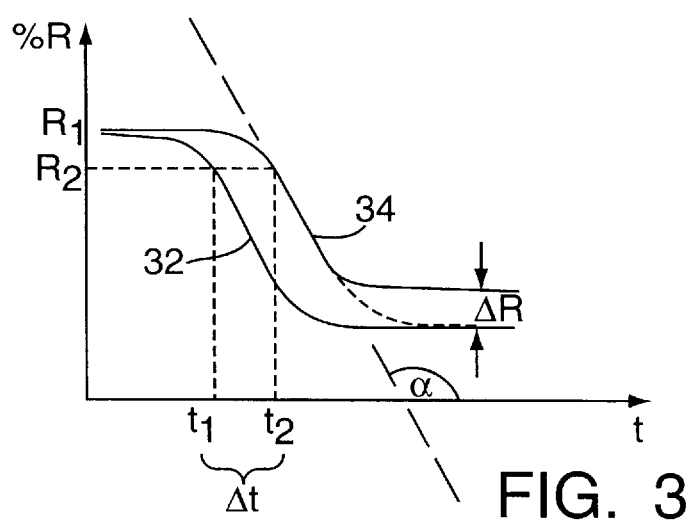

If the indicator device 20 produces a warning indication, this can mean that the test strip 12 has not been inserted up to the stop 21 and that the two measuring areas 26 and 24, therefore, do not lie entirely inside of the measuring field 14. This is especially the case if, after a long time the difference value $\Delta R$ between the two curves 32 and 43 exceeds a given value (FIG. 3).

Further, it can be determined by the rate of change, that is the slope as measured by the angle $\alpha$ of the curves 32 and 34 with respect to the abscissa, which reaction occurs, i.e. which tests are to be carried out, since the reaction kinetics is different from test to test.

It will be understood that the apparatus of FIG. 1 can be modified to have the detector 30 detect light transmitted through the test field 14 rather than light reflected from the test field; and in FIG. 6 such a modification of the FIG. 1 apparatus is illustrated.

Figure 4:
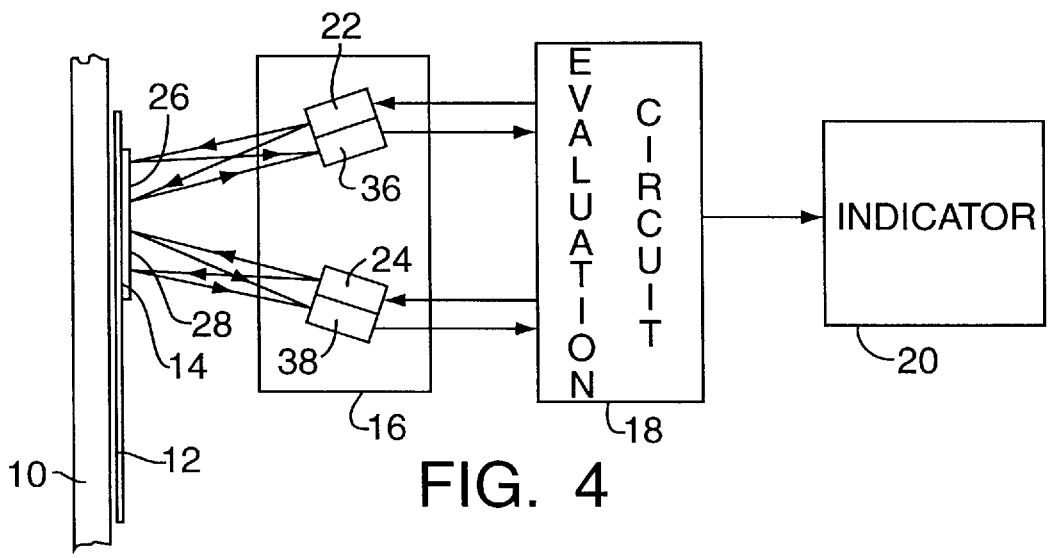
Figure 5:
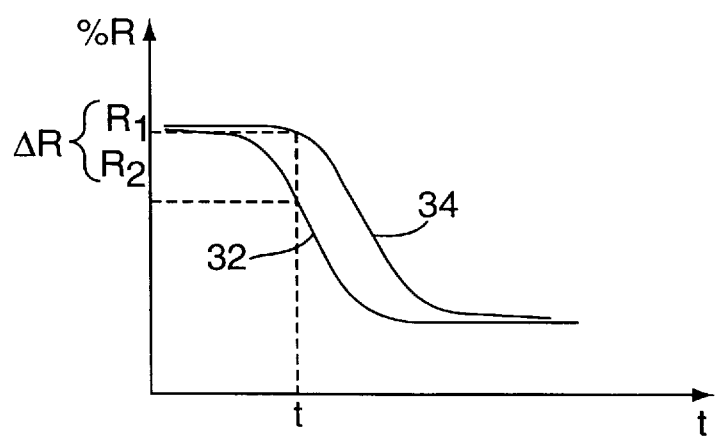

In the embodiment illustrated in FIG. 4, the measuring optic system includes two completely separated sensing units, with each light source 22, 24 having arranged with it an individual detector 36 and 38, and with each detector 36, 38 in this case being so arranged that it detects only the associated measuring area 26 or 28. This solution offers the possibility that both measuring areas 26 and 28 can be simultaneously illuminated and measured. If the measurement for a given time point t produces a $\Delta R = R1-R2$ (FIG. 5) for the two measuring areas 26 and 28 the comparison with a pre-given threshold value $\Delta R$ can again produce a warning signal for the user to apply a subsequent dosage of blood. A further threshold value for $\Delta R$ can be given, upon the exceeding of which a further dosage application is no longer sensible and the measurement must be repeated in its entirety.

I claim:

1. A method for measuring the concentration of a substance in a fluid wherein the measuring fluid is applied to a measuring field (14), consisting of hydrophilic material, of a test strip (12) and the change of the optical reflection or transmission capacity in the area of the measuring field (14) effected thereby is detected, characterized in that the measuring field (14) is divided into at least two measuring areas (26,28), which are separately measured, and that an indicator (20) is actuated, when after a pre-given time (t1, t2; t) the difference of the measured values of the two measuring areas (26, 28) exceeds a pre-determined value, to indicate that the measuring field has not been uniformly wetted.

2. The method according to claim 1, characterized in that the two measuring areas (26, 28) are measured at the same pre-given time point (t) and that the measured values (R1, R2) are compared with one another.

3. The method according to claim 1, characterized in that for each measuring area (26, 28) the time (t1, t2) is measured which is necessary for the change in the reflection or transmission capacity to reach a pre-given value (R2) and that upon the exceeding of a pre-given time interval Δt an indicator (20) is actuated.

4. The method according to claim 1, characterized in that the change of the reflection and transmission capacity over time and size of the measuring areas (26, 28) is determined and an indicator (20) is actuated if the sensed change of the reflection or transmission capacity deviates from a pre-given set value by more than a pre-given amount.

5. An apparatus for measuring the concentration of a substance in a liquid, by means of optical evaluation of a measuring field (14) of a test strip (12) containing the fluid to be measured, including a strip support (10) for the test strip (20), a measuring optic system (16), an evaluation circuit (18) and an indicator unit (12), characterized in that the measuring optic system (16) has at least two sensing units (22, 24, 30; 22, 36, 24, 38) for sensing at least two different measuring areas (26, 28) to produce measured values for each of said two measuring areas, and in that the evaluation circuit (18) produces a signal, indicated by the indicator unit (20), when the difference between said two measured values for said two measuring areas exceeds a predetermined value, to indicate that the measuring field has not been uniformly wetted.

6. An apparatus according to claim 5, characterized in that each of the sensing units has a light emitter and a light receiving unit (22, 36; 24, 38) which are directed onto the different measuring areas (26, 28) and are simultaneously actuatable.

7. An apparatus according to claim 5, characterized in that the sensing units each have a light emitter (22, 24) which is directed onto the different measuring areas (26, 28) and which are actuatable at different time points and that the measuring field (14) is sensed by a common detector (30) of the sensing unit.

* * * * *